United States Patent [19]

Hall et al.

[11] 4,275,202

[45] Jun. 23, 1981

[54] PRODUCTION OF A PURIFIED CYANURIC ACID DIHYDRATE

[75] Inventors: Richard E. Hall, Trenton; Basil A. Guiliano, Plainsboro, both of N.J.

[73] Assignee: FMC Corporation, Philadelphia, Pa.

[21] Appl. No.: 170,280

[22] Filed: Jul. 18, 1980

[51] Int. Cl.³ .......................................... C07D 251/32
[52] U.S. Cl. .................................................. 544/192
[58] Field of Search ........................................ 544/192

[56] References Cited

U.S. PATENT DOCUMENTS

| 2,527,316 | 10/1950 | Mackay | 544/192 |
| 3,107,244 | 10/1963 | Robertson | 544/192 |
| 3,994,892 | 11/1976 | Den Otter et al. | 544/192 |

*Primary Examiner*—John M. Ford
*Attorney, Agent, or Firm*—John J. Jones; Frank Ianno

[57] ABSTRACT

Anhydrous cyanuric acid containing amounts of occluded solvent is recrystallized to a purified cyanuric acid dihydrate by slurrying the contaminated anhydrous cyanuric acid in an aqueous medium.

16 Claims, No Drawings

PRODUCTION OF A PURIFIED CYANURIC ACID DIHYDRATE

This invention relates to the production of a purified cyanuric acid dihydrate, and more particularly relates to the production of a purified cyanuric acid dihydrate from anhydrous cyanuric acid containing occluded solvent as an impurity.

The main use for anhydrous cyanuric acid and cyanuric acid dihydrate is in the preparation of chloro substituted derivatives of isocyanuric acid such as sodium dichloroisocyanurate, potassium dichloroisocyanurate, trichloroisocyanuric acid, and their respective hydrates. These derivative compounds have found extensive use in automatic dishwasher formulations, bleach formulations and in swimming pool disinfection.

Anhydrous cyanuric acid is generally considered to exist in equilibrium as a keto-enol tautomer represented structurally as follows:

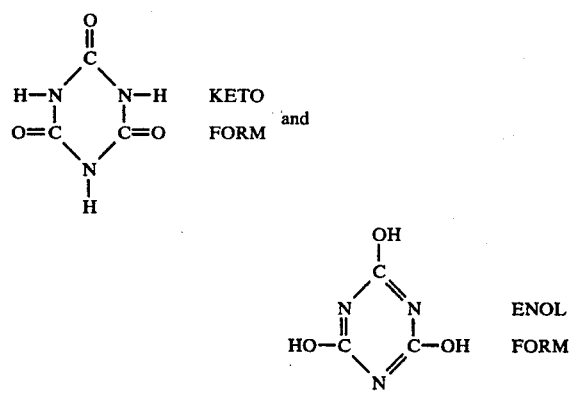

The preparation of anhydrous cyanuric acid is well-known in the art. The basic commercial process involves the pyrolytic deamination of urea over several hours. The reaction can be expressed by the chemical equation:

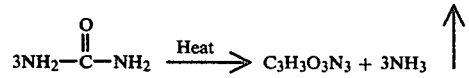

This reaction can be carried out in a dry system, that is, in the absence of a solvent, or it can be carried out in a solvent system wherein the urea is dissolved in a suitable solvent and the resulting solution is heated to effect the conversion of the urea to cyanuric acid. Many solvent systems have been disclosed in the patent literature. Basically, the solvent used must be capable of dissolving urea or biuret in substantial quantities, and the anhydrous cyanuric acid must be relatively insoluble therein. Examples of suitable solvents are the alkyl sulfones disclosed in U.S. Pat. No. 3,065,233, issued to Hopkins et al; and the solvents of the general formula:

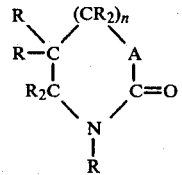

wherein R is hydrogen or a lower alkyl group containing 1–4 carbon atoms, R' is hydrogen, a lower alkyl group containing 1–4 carbon atoms, or phenyl, A is an oxygen atom or $CR_2$, R being as defined above, and n is zero or one when A is oxygen and n is zero when A is $CR_2$, as disclosed in U.S. Pat. No. 3,164,591, issued to Walles, et al. The compounds of Walles, et al would include 5-methyl-2-oxazolidinone, 5-phenyl-2-oxazolidinone, 2-pyrrolidinone, and many others.

Following the production of anhydrous cyanuric acid in a solvent system, the reaction mixture would contain solid anhydrous cyanuric acid, the solvent, some dissolved anhydrous cyanuric acid depending upon the solvent and its temperature, biuret, and unreacted urea, from which the solid anhydrous cyanuric acid must be separated.

Upon separation of the solid anhydrous cyanuric acid from the solvent reaction mixture, the solid anhydrous cyanuric acid contains occluded amounts of solvent which are very difficult to remove. U.S. Pat. No. 3,994,892, issued Nov. 30, 1976 to Den Otter et al, purports to remove occluded solvent by stirring up the contaminated anhydrous cyanuric acid under conditions not requiring recrystallization. Applicants have found that the portion of solvent remaining occluded in the anhydrous cyanuric acid purified by a process without recrystallization is still too high for many applications. For example, the presence of small amounts of sulfolane in the anhydrous cyanuric acid may create some environmental problems in subsequent chlorination operations because the sulfolane becomes chlorinated and is not readily biodegradable.

It has now been discovered that a purified cyanuric acid dihydrate can be produced from an anhydrous cyanuric acid contaminated with amounts of occluded solvent by recrystallizing substantially all of the contaminated anhydrous cyanuric acid in an aqueous medium under conditions sufficient to form the cyanuric acid dihydrate.

In carrying out the present invention, anhydrous cyanuric acid, contaminated with occluded amounts of solvent, is recrystallized to cyanuric acid dihydrate, thereby providing a means of freeing the occluded solvent from the crystal structure of the anhydrous cyanuric acid.

The anhydrous cyanuric acid containing amounts of occluded solvent is slurried in an aqueous medium. This aqueous medium can be water, or mixtures of water and water soluble solvents which do not react with either the anhydrous cyanuric acid or the cyanuric acid dihydrate. Of course, the water soluble solvent can be the same solvent as that occluded within the anhydrous cyanuric acid.

In order to carry out the recrystallization of substantially all of the anhydrous cyanuric acid to form the dihydrate, the aqueous slurry should be maintained at temperatures below about 57° C. for at least about 0.5 hours and preferably for about 1 to about 3 hours. At temperatures higher than about 57° C., the dihydrate will not be produced and the purification resulting from conversion to the dihydrate will not occur.

The size of the crystalline anhydrous cyanuric acid influences the rate of hydration to the cyanuric acid dihydrate. The larger the crystals, the slower the rate of hydration because of the smaller surface area as compared to an equal weight of smaller crystals. Generally, the crystals of anhydrous cyanuric acid produced in a solvent process will require from about 1 to about 3 hours to achieve a substantial recrystallization to cyanuric acid dihydrate. This time can be favorably decreased to from about 0.5 hours to about 0.75 hours by grinding the anhydrous crystals prior to carrying out the recrystallization.

Preferably the temperature of the aqueous slurry should be maintained at ambient temperatures to minimize energy costs.

The solvent occluded within the anhydrous cyanuric acid may be any solvent which is, to some degree, soluble in water at temperatures below about 57° C. Included, for example, are the alkyl sulfones disclosed by Hopkins et al, supra, such as dimethylsulfone, dipropylsulfone, sulfolane and its derivatives, and the solvents disclosed by Walles et al, supra, such as 5-methyl-2-oxazolidinone, 5-phenyl-2-oxazolidinone, 2-pyrrolidinone.

During the recrystallization, the slurry is vigorously agitated to keep the solids in suspension and off the bottom of the recrystallization vessel.

Following the recrystallization, the cyanuric acid dihydrate crystals are separated from the aqueous medium by any conventional solid-liquid separation means, such as by filtration, centrifugation, decantation and the like.

The separated crystals are then preferably washed one or more times with pure water. The amount of wash water should be kept below three pounds of water per pound of cyanuric acid dihydrate, and preferably below two pounds of water per pound of cyanuric acid dihydrate to limit the losses of cyanuric acid dihydrate due to dissolution. The wet cyanuric acid dihydrate may then, for example, be dissolved in water and used as feed to a chlorination operation, or it may even be dried to provide anhydrous cyanuric acid.

We claim:

1. A process for the production of a purified cyanuric acid dihydrate from anhydrous cyanuric acid contaminated with amounts of occluded solvent which comprises recrystallizing substantially all of the contaminated anhydrous cyanuric acid in an aqueous medium under conditions sufficient to form the cyanuric acid dihydrate.

2. The process of claim 1 wherein the recrystallization is conducted at a temperature below about 57° C.

3. The process of claim 2 wherein the temperature is about ambient temperature.

4. The process of claim 1 wherein the recrystallization takes at least about 0.5 hours.

5. The process of claim 1 further comprising grinding the anhydrous cyanuric acid prior to recrystallizing.

6. The process of claim 5 wherein the recrystallization takes from about 0.5 to about 0.75 hours.

7. The process of claim 1 wherein the occluded solvent is sulfonane.

8. The process of claim 1 wherein the aqueous medium is water mixed with a water soluble solvent.

9. The process of claim 8 wherein the water soluble solvent and the occluded solvent are the same.

10. The process of claim 9 wherein the water soluble solvent and the occluded solvent are sulfolane.

11. A process for the production of a purified cyanuric acid dihydrate from an anhydrous cyanuric acid contaminated with amounts of occluded sulfolane which comprises recrystallizing at about ambient temperature substantially all of the contaminated anhydrous cyanuric acid in an aqueous medium of water and sulfolane under conditions sufficient to form the cyanuric acid dihydrate, separating the cyanuric acid dihydrate from the aqueous medium, and washing the cyanuric acid dihydrate with water.

12. The process of claim 11 wherein the separation is conducted by filtration.

13. The process of claim 11 wherein the separation is conducted by centrifugation.

14. The process of claim 11 wherein the washing is conducted using no more than about 3 parts by weight of water per part of cyanuric acid dihydrate.

15. The process of claim 11 wherein the washing is conducted using from about 1 to about 2 parts by weight of water per part of cyanuric acid dihydrate.

16. The process of claim 11 wherein the recrystallization takes from about 1 to about 3 hours.

* * * * *

UNITED STATES PATENT AND TRADEMARK OFFICE
CERTIFICATE OF CORRECTION

PATENT NO. : 4,275,202
DATED : June 23, 1981
INVENTOR(S) : Richard E. Hall and Basil A. Builiano It is certified that error appears in the above—identified patent and that said Letters Patent is hereby corrected as shown below:

Column 4, line 17, claim 7, "sulfonane" should read --sulfolane--

Signed and Sealed this

Twenty-second Day of September 1981

[SEAL]

Attest:

GERALD J. MOSSINGHOFF

Attesting Officer

Commissioner of Patents and Trademarks